(12) United States Patent
Ernsberger et al.

(10) Patent No.: US 7,812,098 B2
(45) Date of Patent: Oct. 12, 2010

(54) BEARING MATERIAL OF MEDICAL IMPLANT HAVING REDUCED WEAR RATE AND METHOD FOR REDUCING WEAR RATE

(75) Inventors: Craig Ernsberger, Granger, IN (US); Yen-Shuo Liao, Warsaw, IN (US); Lawrence Salvati, Goshen, IN (US)

(73) Assignee: Depuy Products, Inc., Warsaw, IN (US)

( * ) Notice: Subject to any disclaimer, the term of this patent is extended or adjusted under 35 U.S.C. 154(b) by 884 days.

(21) Appl. No.: 11/394,423

(22) Filed: Mar. 31, 2006

(65) Prior Publication Data

US 2007/0232761 A1   Oct. 4, 2007

(51) Int. Cl.
C08F 10/00 (2006.01)

(52) U.S. Cl. .............. 525/333.7; 428/339; 428/500; 428/523; 264/241; 623/11.11; 623/23.58; 623/23.59; 623/23.6

(58) Field of Classification Search .............. 623/23.58, 623/23.59, 23.6; 428/339, 500, 523; 264/241
See application file for complete search history.

(56) References Cited

U.S. PATENT DOCUMENTS

| | | | |
|---|---|---|---|
| 3,297,805 A | 1/1967 | Rottig et al. | |
| 3,954,927 A | 5/1976 | Duling et al. | |
| 4,454,612 A | 6/1984 | McDaniel et al. | |
| 4,670,508 A | 6/1987 | Ohdaira et al. | |
| 4,778,601 A | 10/1988 | Lopatin et al. | |
| 4,880,843 A | 11/1989 | Stein | |
| 5,082,655 A * | 1/1992 | Snipes et al. | 424/486 |
| 5,275,838 A | 1/1994 | Merrill | |
| 5,288,818 A | 2/1994 | Livingston, Jr. et al. | |
| 5,414,049 A | 5/1995 | Sun et al. | |
| 5,489,303 A | 2/1996 | Sasaki et al. | |
| 5,593,719 A | 1/1997 | Dearnaley et al. | |
| 5,594,055 A | 1/1997 | Young | |
| 5,641,502 A * | 6/1997 | Skalla et al. | 424/426 |
| 5,721,334 A | 2/1998 | Burstein et al. | |
| 5,807,502 A | 9/1998 | Wollenweber et al. | |
| 5,827,904 A | 10/1998 | Hahn | |
| 5,844,027 A | 12/1998 | Burdick et al. | |
| 5,879,400 A | 3/1999 | Merrill et al. | |
| 5,945,457 A | 8/1999 | Plate et al. | |
| 6,017,975 A | 1/2000 | Saum et al. | |
| 6,123,990 A | 9/2000 | Wiggins et al. | |
| 6,133,249 A | 10/2000 | Hills | |
| 6,174,934 B1 | 1/2001 | Sun et al. | |
| 6,228,900 B1 | 5/2001 | Shen et al. | |
| 6,242,507 B1 | 6/2001 | Saum et al. | |
| 6,277,390 B1 | 8/2001 | Schaffner | |
| 6,281,264 B1 | 8/2001 | Salovey et al. | |
| 6,316,158 B1 | 11/2001 | Saum et al. | |
| 6,365,089 B1 | 4/2002 | Krebs et al. | |
| 6,379,741 B1 | 4/2002 | Komvopoulos et al. | |
| 6,395,799 B1 | 5/2002 | Johnson | |
| 6,448,315 B1 | 9/2002 | Lidgren et al. | |
| 6,494,917 B1 | 12/2002 | McKellop et al. | |
| 6,800,670 B2 | 10/2004 | Shen et al. | |
| 6,818,172 B2 | 11/2004 | King et al. | |
| 6,846,875 B2 | 1/2005 | Pennings et al. | |
| 6,916,857 B2 | 7/2005 | Won et al. | |
| 7,335,697 B2 * | 2/2008 | King et al. | 524/585 |
| 2002/0125614 A1 | 9/2002 | King et al. | |
| 2003/0083433 A1 | 5/2003 | James et al. | |
| 2003/0125513 A1 | 7/2003 | King | |
| 2003/0144741 A1 | 7/2003 | King et al. | |
| 2003/0144742 A1 | 7/2003 | King et al. | |
| 2003/0149125 A1 | 8/2003 | Muratoglu et al. | |
| 2003/0193110 A1 | 10/2003 | Yaritz et al. | |
| 2003/0212161 A1 | 11/2003 | McKellop et al. | |
| 2004/0068322 A1 | 4/2004 | Ferree | |
| 2004/0156879 A1 | 8/2004 | Muratoglu et al. | |
| 2004/0210316 A1 | 10/2004 | King et al. | |
| 2004/0243249 A1 | 12/2004 | Ishihara et al. | |
| 2004/0262809 A1 | 12/2004 | Smith et al. | |
| 2004/0265165 A1 | 12/2004 | King | |
| 2004/0266903 A1 | 12/2004 | King | |

(Continued)

FOREIGN PATENT DOCUMENTS

DE          227 328 A     9/1985

(Continued)

OTHER PUBLICATIONS

European Patent Office, Extended European Search Report in European Patent Application No. 07251351.8-1219 (DePuy Products, Inc.) (Dec. 3, 2007).

(Continued)

Primary Examiner—Vasu Jagannathan
Assistant Examiner—Robert C Boyle (57) ABSTRACT

Disclosed is a bearing material of a medical implant comprising a polymer such as UHMWPE and a surface active agent that is not covalently bonded to the polymer. The bearing material has a reduced wear rate. Also disclosed is a method of reducing the wear rate of a polymeric bearing material of a medical implant when it articulates against a hard counterface in the presence of synovial fluid, the method comprising providing a surface active agent in the synovial fluid in close proximity to the bearing surface, the hard counterface, or both.

21 Claims, 4 Drawing Sheets

U.S. PATENT DOCUMENTS

| | | | |
|---|---|---|---|
| 2005/0019366 A1 | 1/2005 | Zeldis | |
| 2005/0065307 A1* | 3/2005 | King et al. | 526/352 |
| 2005/0069696 A1* | 3/2005 | King et al. | 428/339 |
| 2006/0004168 A1 | 1/2006 | Greer et al. | |
| 2006/0149387 A1 | 7/2006 | Smith et al. | |
| 2006/0149388 A1 | 7/2006 | Smith et al. | |

FOREIGN PATENT DOCUMENTS

| | | |
|---|---|---|
| DE | 19750121 C1 | 4/1999 |
| EP | 0047171 A2 | 3/1982 |
| EP | 0 335 613 A | 10/1989 |
| EP | 0681845 A2 | 11/1995 |
| EP | 0730001 A1 | 9/1996 |
| EP | 0805178 A1 | 11/1997 |
| EP | 1086709 A1 | 3/2001 |
| EP | 1493775 A1 | 1/2005 |
| EP | 1520877 A1 | 4/2005 |
| EP | 1779876 A3 | 5/2007 |
| EP | 1839685 A2 | 10/2007 |
| JP | 48-054168 A | 7/1973 |
| JP | 60-252645 A | 12/1985 |
| WO | WO 85/04365 A | 10/1985 |
| WO | WO 86/02656 A | 5/1986 |
| WO | 89/01777 A | 3/1989 |
| WO | WO 93/25247 A | 12/1993 |
| WO | 95/26169 A | 10/1995 |
| WO | WO 97/29895 A1 | 8/1997 |
| WO | 98/01085 A | 1/1998 |
| WO | WO 00/49079 A1 | 8/2000 |
| WO | 01/85179 A | 11/2001 |
| WO | WO 02/26464 A1 | 4/2002 |
| WO | WO 03/057769 A | 7/2003 |
| WO | WO 03/087217 A1 | 10/2003 |
| WO | WO 2004/032987 A1 | 4/2004 |
| WO | WO 2004/064618 A | 8/2004 |
| WO | WO 2004/071451 A2 | 8/2004 |

OTHER PUBLICATIONS

Hills, "Remarkable anti-wear properties of joint surfactant," *Ann. Biomed. Eng.*, 23: 112-115 (1995).

Moro et al., "Surface grafting of artificial joints with a biocomppatible polymer for preventing periprosthetic osteolysis," *Nat. Mater.*, 3: 829-836 (Nov. 2004).

Bavaresco et al., "Devices for use as an artificial articular surface in joint prostheses or in the repair of osteochondral defects," *Artif. Organs*, 24 (3), 202-205 (Mar. 2000).

Beauregard et al., "Synthesis and characterization of a novel UHMWPE interpenetrating polymer network," *Biomed. Sci. Instrum.*, 35, 415-419 (Apr. 16, 1999).

Heuberger et al., "Protein-mediated boundary lubrication in arthroplasty," *Biomaterials*, 26 (10), 1165-1173 (Apr. 2005).

King et al., "Hydrophilic, porous ultra-high molecular weight polyethylene for orthopaedic implants," *7th World Biomaterials Congress Transactions*, 1909 (May 17-21, 2004).

Kurtz et al., "Advances in the processing, sterilization, and crosslinking of ultra-high molecular weight polyethylene for total joint arthroplasty," *Biomaterials*, 20 (18), 1659-1688 (Sep. 1999).

Paul, "Forces transmitted by joints in the human body," *Proc. Inst. Mech. Eng.*, 181 (3J), 8-15 (1966-1967).

Shutov et al., "Cellular UHMW polyethylene produced by non-foaming leaching technique: morphology and properties," *J. Cel. Plast.*, 38 (Part 2), 163-176 (2002).

Stein, "Ultra high molecular weight polyethylene (UHMWPE)," in *Engineered Materials Handbook vol. 2: Engineering Plastics*, 167-171 (1998).

Wang et al., "The impact of lubricant protein concentration on the outcome of hip joint simulator wear testing," *Society for Biomaterials Annual Meeting in Conjunction with the International Biomaterials Symposium*, 22, 178 (1999).

Zhang et al., "Surface modification of UHMWPE for use in total joint replacements," *Biomed. Sci. Instrum.*, 40, 13-17 (2004).

Barr et al., "EPR as a quality control method for the release of cross-linked ultra high molecular weight polyethylene," *Bruker Epr Application Note*, 1-3 (Bruker Instruments, Inc., Billerica, Massachusetts, Feb. 28, 2003).

European Patent Office, Search Report in European Patent Application No. 06255075.1 (Mar. 30, 2007).

European Patent Office, Search Report in European Patent Application No. 07252847.4 (Mar. 3, 2008).

Oral et al., "α-Tocopherol-doped irradiated UHMWPE for high fatigue resistance and low wear," *Biomaterials*, 25 (24): 5515-5522 (2004).

Tadros, "Surfactants," in Kirk-Othmer Encyclopedia of Chemical Technology, Fifth Edition (Seidel, ed.), 118-161 (John Wiley & Sons, Inc., Hoboken, New Jersey, USA, 2007).

Veiga-Crespo et al., "Influence of culture conditions of Gordonia jacobaea MV-26 on canthaxanthin production," *Int. Microbiol.*, 8 (1): 55-58 (Mar. 2005).

Zhang et al., "A novel ultra high molecular weight polyethylene-hyaluronan microcomposite for use in total joint replacements. I. Synthesis and physical/chemical characterization," *J. Biomed. Mater. Res. A*, 78A, 86-96 (Apr. 2006).

* cited by examiner

BEARING MATERIAL OF MEDICAL IMPLANT HAVING REDUCED WEAR RATE AND METHOD FOR REDUCING WEAR RATE

BACKGROUND OF THE INVENTION

Medical implants employ a polymeric material such as ultrahigh molecular weight polyethylene (UHMWPE) as the bearing material which articulates against a hard counterface, for example, a metallic counterface, of the implant. The polymeric material, however, tends to wear during use with concomitant production of wear debris comprising microscopic particles of the polymer. These particles can cause adverse reactions such as inflammation and deterioration of cell tissues, or osteolysis of the tissues.

Attempts have been made to reduce the wear rate of the bearing material, particularly UHMWPE, for example, by modifying the bulk properties of the polymer. Approaches to modify the bulk properties of the bearing material include radiation crosslinking of the polymer and stabilizing the associated free radicals against oxidation. While highly crosslinked UHMWPE has wear rates lower than the uncrosslinked material, the highly crosslinked material also tends to produce finer wear debris with higher osteolytic potential.

The foregoing shows that there exists a need for a medical implant or medical implant part, such as the bearing material, which has a reduced wear rate. The present invention provides such an implant or implant part. The present invention also provides a method for reducing the wear rate.

BRIEF SUMMARY OF THE INVENTION

The invention provides a bearing material of a medical implant comprising a polymer such as UHMWPE and a surface active agent that is not covalently bonded to the polymer. The bearing material has a reduced wear rate; it produces a reduced amount of wear debris. The bearing material can offer reduced osteolysis. The surface active agent acts as a boundary lubricant, and reduces the friction between the polymer of the bearing material when it articulates against the hard counterface. The bearing material of the invention has one or more advantages. For example, the bearing material of the invention made of UHMWPE and containing a surface agent provides a lower wear rate than a bearing material made of crosslinked UHMWPE.

The present invention also provides a method of reducing the wear rate of a polymeric bearing material of a medical implant when it articulates against a hard counterface in the presence of synovial fluid, the method comprising providing a surface active agent in the synovial fluid in close proximity to the bearing surface, the hard counterface, or both.

DETAILED DESCRIPTION OF THE INVENTION

The present invention is predicated on the observation that surface active agents reduce the friction, and/or provide a lubricating effect, between a polymer surface articulating against a hard counterface in a fluid medium such as serum containing a protein. Accordingly, in an embodiment, the invention provides a bearing material of a medical implant comprising a polymer and a surface active agent that is not covalently bonded to the polymer, wherein the bearing material is adopted for articulating against a hard counterface of the medical implant.

The bearing material in accordance with the invention can be that of any suitable medical implant or medical implant part. Suitable medical implants or medical implant parts include, but are not limited to, the acetabular cup, the insert or liner of the acetabular cup, or trunnion bearings (e.g., between the modular head and the stem) of artificial hip joints, the tibial plateau, patellar button (patello-femoral articulation), and trunnion or other bearing components of artificial knee joints, the talar surface (tibiotalar articulation) and other bearing components of artificial ankle joints, the radio-numeral joint, ulno-humeral joint, and other bearing components of artificial elbow joints, the glenoro-humeral articulation and other bearing components of artificial shoulder joints, intervertebral disk replacements and facet joint replacements for the spine, temporo-mandibular joints (jaw), and finger joints.

The polymer of the bearing material can be made of any suitable polymer, specifically polyethylene, particularly ultrahigh molecular weight polyethylene (UHMWPE), which typically has a weight average molecular weight of about 400,000 atomic mass units or more. As utilized herein, the term "ultrahigh molecular weight polyethylene" refers to a polyethylene polymer having a weight average molecular weight of about 400,000 atomic mass units or more. Preferably, the ultrahigh molecular weight polyethylene has a weight average molecular weight of about 1,000,000 (e.g., about 2,000,000 or about 3,000,000) atomic mass units or more. Typically, the weight average molecular weight of the ultrahigh molecular weight polyethylene is less than 10,000,000 atomic mass units or less, more preferably about 6,000,000 atomic mass units or less. Ultrahigh molecular weight polyethylene suitable for use in the invention includes, but is not limited to, commercially available ultrahigh molecular weight polyethylene, such as GUR 1050 (weight average molecular weight of about 5,000,000 to about 6,000,000 atomic mass units) or GUR 1020 (weight average molecular weight of about 3,000,000 to about 4,000,000 atomic mass units) powdered ultrahigh molecular weight polyethylene from Ticona (Summit, N.J.).

The surface active agent, which contains both hydrophobic and hydrophilic segments, can be any suitable surface active agent, for example, anionic, cationic, nonionic, or amphoteric, preferably nonionic. The surface active agent is an added (endogenous) surface active agent, and does not refer to any surface active agent that may be present in the synovial fluid naturally. The surface active agent can be of any suitable molecular weight, for example, from about 100 to about 20,000 g/mole or more, and in embodiments from about 1000 to about 20,000 g/mole. In an embodiment, the nonionic surface active agent comprises a block copolymer of hydrophilic and hydrophobic blocks, for example, the surface active agent is block copolymer of the type A-B, A-B-A, or B-A-B or a combination thereof, wherein A is a hydrophilic block and B is a hydrophobic block. As an example, A is polyethylene oxide (PEO) and B is polypropylene oxide (PPO). In an embodiment, the surface active agent is PLURONIC™ F127, available from BASF, which has a molecular weight of about 12,600 g/mole.

The surface active agent can be incorporated into the bearing material in any suitable amount, for example, in an amount of about 0.01% by weight or more, e.g., from about 0.1% to about 5%, and preferably from about 0.5% to about 1% by weight of the bearing material.

The wear rate of the polymer, particularly UHMWPE, is reduced at least by a factor of about 2, preferably 5, and more preferably about 10, relative to the unmodified polymer, particularly when the surface active agent is added at a level of 1% to the fluid, e.g., synovial fluid or serum. For example, PLURONIC F127 reduces the wear rate of UHMWPE by a factor of 10 when added to the serum at a level of 1% by weight of the serum. Wear rate and the coefficient of friction can be determined by methods known in the art, for example, by measuring the loss of weight or the normal force in the Pin-on-Disk method.

The invention further provides a method of reducing the wear rate of a polymeric bearing material of a medical implant, the bearing material having a bearing surface, the bearing surface articulating against a hard counterface of the medical implant in the presence of synovial fluid, the method comprising providing a surface active agent in the synovial fluid in close proximity to the bearing surface, the hard counterface, or both. In an embodiment, the bearing material includes a surface active agent that migrates to the interface between the bearing surface and the synovial fluid.

The surface active agent can be included in the bearing material by any suitable method, for example, by molding, ram extrusion, or infiltration of the finished polymeric (e.g., UHMWPE) article with the surface active agent in a suitable solvent. Thus, for example, powdered or pelletized UHMWPE and a surface active agent can be blended, e.g., dry blended, at a desired concentration and the resulting blend can be molded by compression molding or ram extrusion.

The surface active agent can be originally distributed throughout the bearing material or only present on the small portion thereof, e.g., at the surface. Thus, for example, the surface active agent can be present in a surface layer having a thickness of about 0.5 mm or more, e.g., from about 0.5 mm to about 2 mm or more. The internal volume of the compression mold can be filled entirely with a blend of the polymer and the surface active agent, or alternatively, a portion of the internal volume can be filled with the blend, and the remaining volume filled with the polymer. In the latter case, the surface active agent will be contained in the surface of the bearing material.

Alternatively, the bearing material can be immersed in a solution of the surface active agent at a suitable temperature and for suitable length of time to obtain a sufficient concentration of the surface active agent in the polymer. The solvent can be removed by suitable drying.

In another embodiment, the hard counterface includes a surface active agent and releases the surface active agent into the synovial fluid in close proximity to the hard counterface. For example, the surface active agent can be included in a hydrogel which can be incorporated into a porous support in close proximity to the articulating surfaces. For example, the hydrogel can be formed from hydrophobic and hydrophilic macromers; see, e.g., U.S. Pat. Nos. 6,916,857 and 6,846,875.

The resulting hydrogel can be loaded with a surface active agent. The hydrogel can be coated on the hard counterface.

In yet another embodiment of the invention, the surface active agent can be provided by injecting the surface active agent into the synovial fluid. If the surface active agent is injected into the fluid, in accordance with an embodiment of the invention, it can be injected, for example, in an amount of about 0.01% by weight or more, e.g., from about 0.1 to about 5%, and preferably from about 0.5 to about 1% by weight of the fluid.

In a further embodiment, the surface active agent can be provided such that it elutes from a non-articulating portion of the medical implant.

Whether the surface active agent is originally present in the serum (or synovial fluid) or in the bulk of the polymer, it migrates to the interface between the polymer and the serum due to the reduction of surface energy.

The hard counterface of the implant can be made of any suitable material, e.g., metallic, ceramic, or a combination thereof. Suitable metals include titanium, tantalum, and stainless steel. Typically, the hard counterfaces are formed from a metallic alloy that will exhibit appropriate strength and flexure in use. Examples of metallic alloys that may be used include titanium alloys, such as a titanium-aluminum-vanadium alloy, and cobalt-chromium alloys, such as a cobalt-chromium-molybdenum alloy, and stainless steel. In a specific example, the hard counterface comprises cobalt-chromium-molybdenum alloy.

Figure 1:
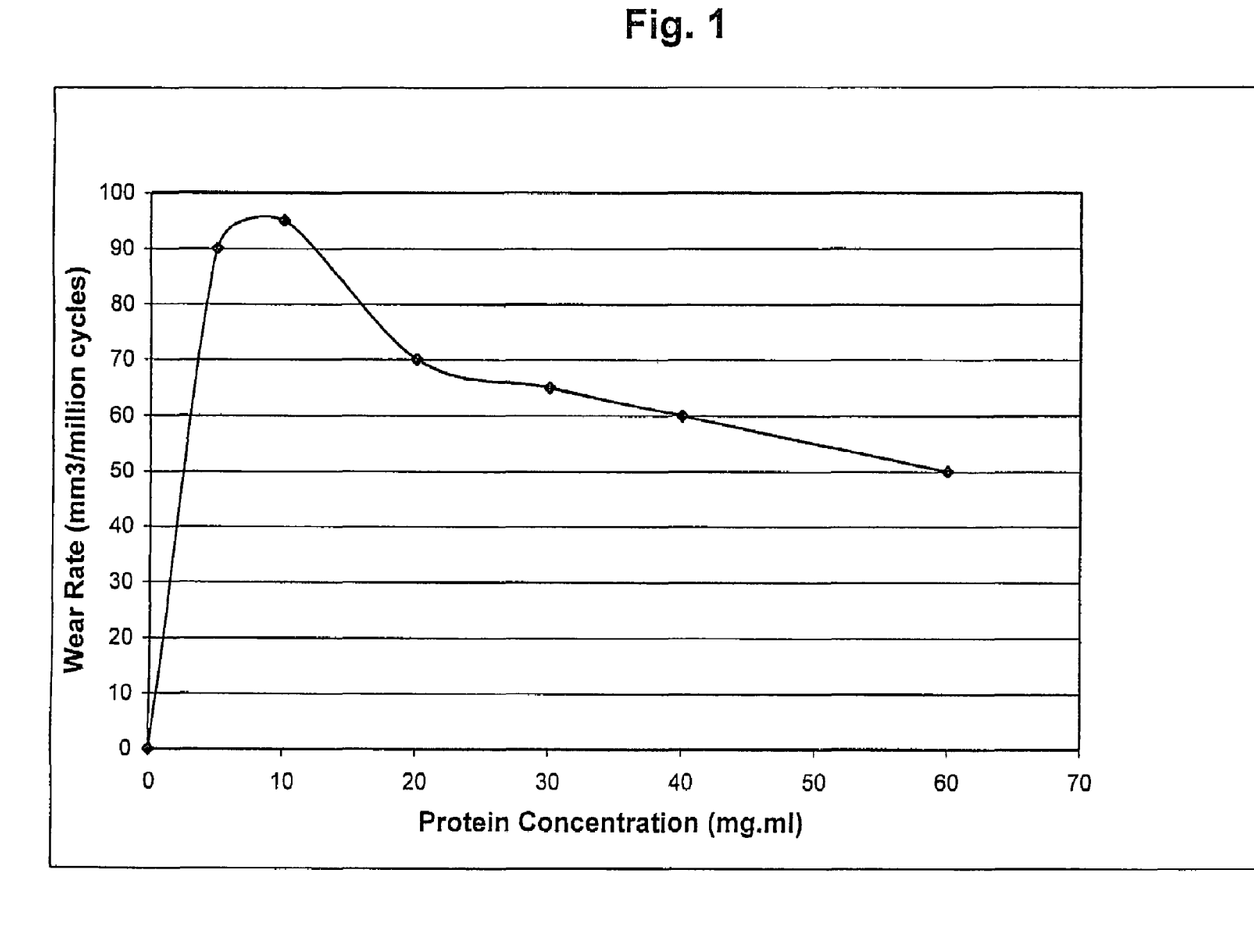
FIG. 1 depicts the known wear rate of UHMWPE bearing material against various counterfaces as a function of the concentration of proteins in the serum.
Figure 2A:
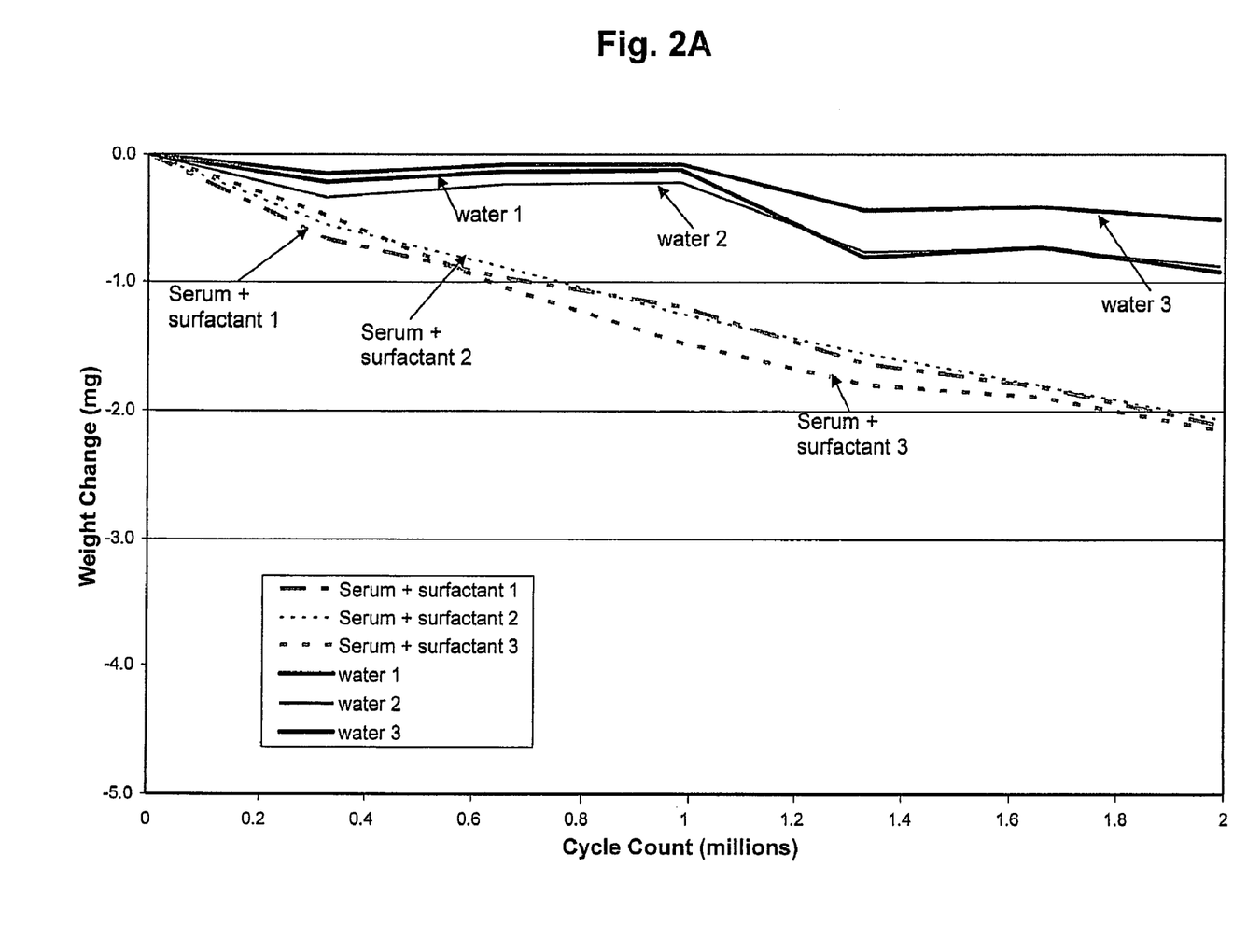
FIG. 2A depicts the weight change of UHMWPE pin as it rubs against cast CoCrMo counterfaces in water and in bovine calf serum plus 1% by weight surface active agent in accordance with an embodiment of the invention.
Figure 2B:
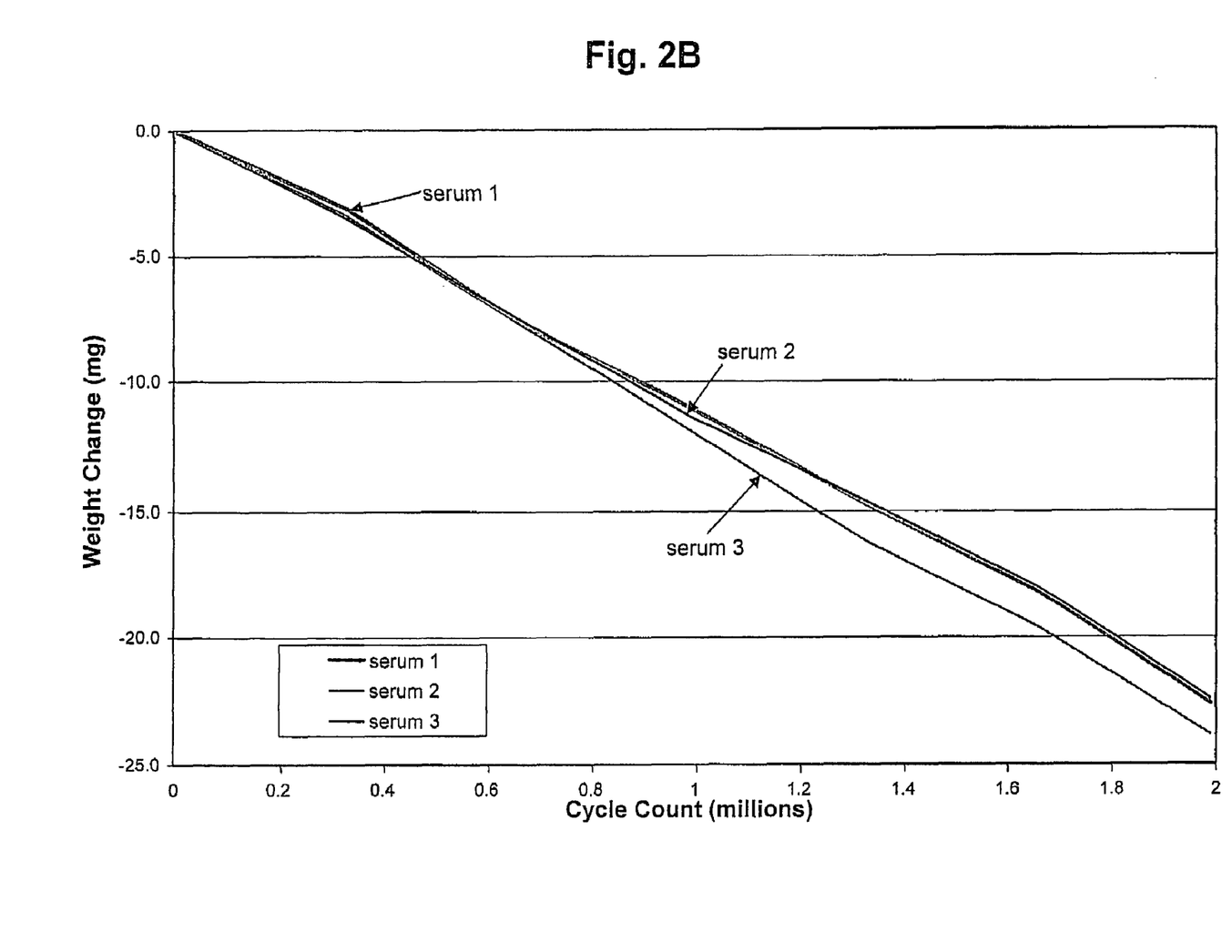
FIG. 2B depicts the weight change of the UHMWPE pins in bovine calf serum only.
Figure 3:
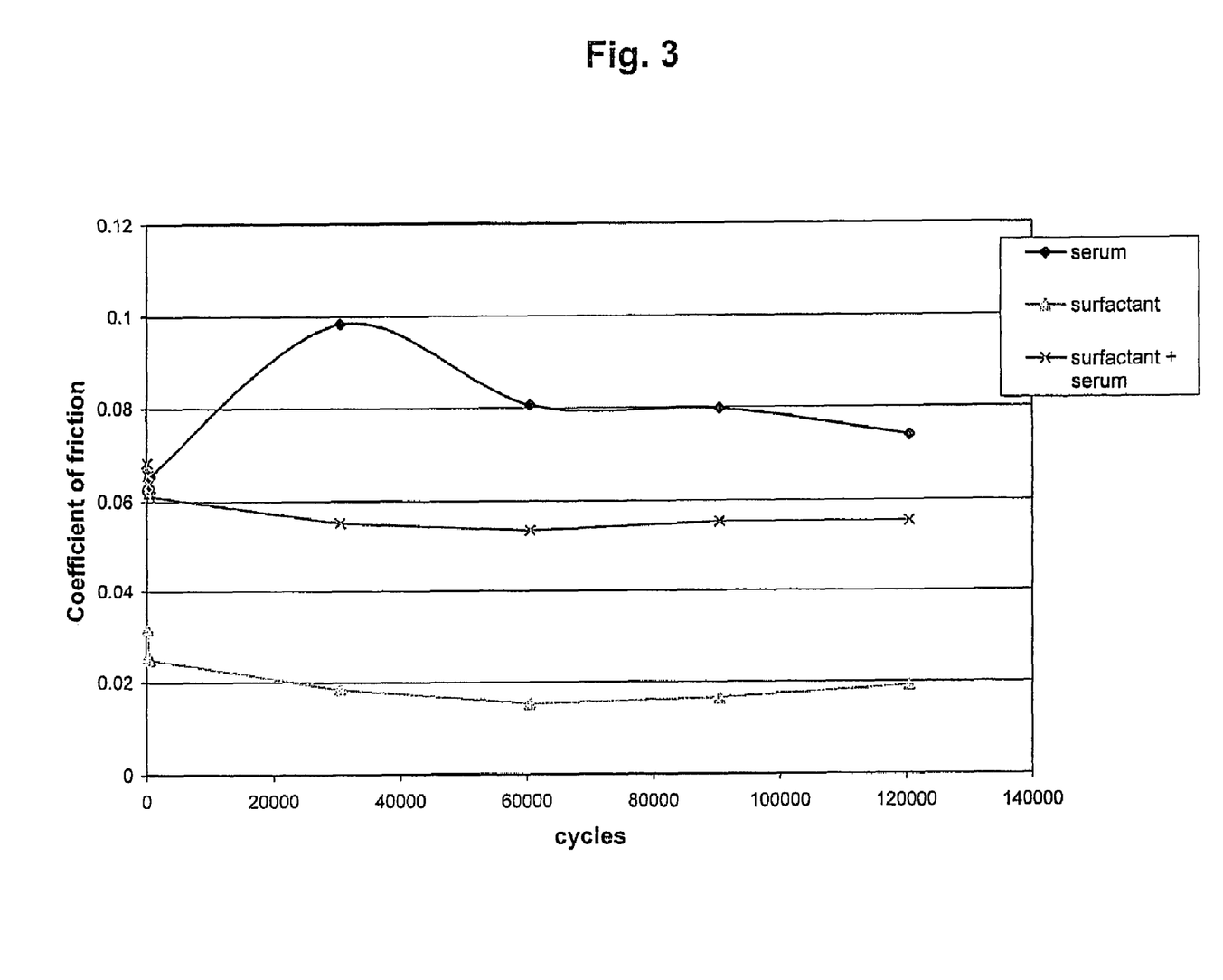
FIG. 3 depicts the coefficient of friction between UHMWPE pins and CoCrMo counterfaces as a function of the number of cycles in serum (diamonds), 1% by weight surface active agent (triangles), and serum plus 1% by weight surface active agent (x), in accordance with an embodiment of the invention.

It is known that proteins tend to alter the wear rate of UHMWPE. For example, as shown in FIG. 1, the wear rate increases with increasing protein concentration up to a certain protein concentration. Beyond this concentration, the wear rate tends to decrease. In accordance with the present invention, by the use of a surface active agent, it is possible to reduce the wear rate even further. As depicted in FIG. 2, the wear rate of UHMWPE in a serum containing 1% surface active agent is less than that in serum alone. Further, as shown in FIG. 3, the coefficient of friction of UHMWPE against Co—Cr—Mo counterface is decreased by the use of a surface active agent in the serum.

The following examples further illustrate the invention but, of course, should not be construed as in any way limiting its scope.

EXAMPLE 1

This example illustrates an advantage of the surface active agent, namely, it reduces the wear rate of UHMWPE.

UHMWPE pins, 0.7 inch long and 0.375 inch diameter, manufactured from GUR 1020 resin is ram extruded into bar stock. The pins are sterilized by irradiation. Metal counterfaces, 1.5 inch diameter and 0.5 inch thick, are fabricated from cast 68% cobalt, 26% chromium, 6% molybdenum, and 0.2% carbon. The counterfaces are hot isostatic pressed and homogenized by heat treatment and polished to an average surface roughness of between 10 and 20 nm. Three disks are obtained for each wear test group. A sample pairing chart including same identifications is shown in Table 1.

TABLE 1

Sample Pairing and Identification.

| Sample Group | Pin | Disk | Station |
|---|---|---|---|
| Serum and surface active agent | S1 | 2B | 1 |
| | S2 | 5B | 2 |
| | S3 | 6 | 3 |

TABLE 1-continued

Sample Pairing and Identification.

| Sample Group | Pin | Disk | Station |
|---|---|---|---|
| Water | W1 | 7 | 4 |
|  | W2 | 8 | 5 |
|  | W3 | 9 | 6 |
| Serum | 4 | 43 | 4 |
|  | 5 | 44 | 5 |
|  | 6 | 45 | 6 |

The wear tests are conducted on a Pin-on-Disk (POD) machine (AMTI OrthoPOD). The pins move in a 10 mm by 10 mm square pattern with respect to the disk, providing a maximum amount of cross shear motion. A Paul loading cycle with a peak of 330N is applied (Paul, J., Forces transmitted by joints in the human body, Proc. Inst. Mech. Eng., 181, 8-15 (1967)). The frequency is 1.6 Hz. Six, 0.33 million-cycle data collection intervals are performed for a 1.98 million cycle test duration. Water lost by evaporation is replenished approximately every 24 hours. The test lubricant is discarded at the end of each test interval, and fresh lubricant is added.

After each data collection interval, each sample pair is rotated clockwise one station for the next interval. During the course of the test all of the samples are tested in all of the stations. Three different lubricants are tested: Reverse Osmosis treated water, Bovine serum (Hyclone Inc. diluted to 90% of the initial concentration and treated with EDTA and sodium azide), and the bovine serum formulation above containing 1% by weight PLURONIC F127 surfactant. Bulk serum temperature is maintained at 37° C.

Gravimetric data is obtained from the pins as follows. The pins are cleaned and weighed in a microbalance with 0.01 mg resolution. The balance is calibrated with standard weights. Corrections for fluid uptake are applied using standard soak control pins. Contact profilometry of the disks is performed on a Taylor-Hobson Form Talysurf Series II Profilometer. A cut off length of 250 microns, a 100:1 bandwidth, and a gauge range of 1 mm are used. Two pairs of perpendicular traces are taken on each sample. Pictures of the pins are taken with a Nikon Epiphot 200/300 Inverted Microscope (metallograph). Pictures of the disks are taken with a Nikon D1 Digital Camera.

FIG. 2A-B depict the wear rate of UHMWPE pins. The wear rate of the pins is less when a surface active agent is employed.

EXAMPLE 2

This example illustrates an advantage of the present invention, namely, the coefficient of friction between the polymer surface and the hard counterface is reduced.

Friction data is collected on the same type of pins and disks illustrated in Example 1. The data are obtained on an AMTI OrthoPOD Pin-on-Disk tester equipped with multiaxis strain gauges. The coefficient of friction is calculated by dividing the normal force by the in plane force during the same 10 mm by 10 mm test pattern and Paul load cycle used in wear testing. The friction data is collected over a small portion of the test pattern between the peaks of the Paul loading curve. FIG. 3 depicts the reduction in the coefficient of friction brought about by the use of the surfactant. Each point in FIG. 3 is the average of approximately 30 data points.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A bearing material of a medical implant comprising ultrahigh molecular weight polyethylene (UHMWPE) and a surface active agent having a molecular weight of from about 100 to about 20,000 g/mole that is not covalently bonded to the UHMWPE, wherein the surface active agent is present in an amount from about 0.1% to about 1% by weight of the bearing material, wherein the bearing material is adapted for articulating against a hard counterface of the medical implant.

2. The bearing material of claim 1, wherein the surface active agent is an anionic, cationic, nonionic, or amphoteric surface active agent.

3. The bearing material of claim 2, wherein the surface active agent is a nonionic surface active agent.

4. The bearing material of claim 3, wherein the nonionic surface active agent comprises a block copolymer of hydrophilic and hydrophobic blocks.

5. The bearing material of claim 4, wherein the block copolymer is an A-B, A-B-A, or B-A-B block copolymer, wherein A is a hydrophilic block and B is a hydrophobic block.

6. The bearing material of claim 5, wherein A is polyethylene oxide (PLO) and B is polypropylene oxide (PPO).

7. The bearing material of claim 6, wherein the molecular weight of the copolymer is from about 1000 to about 20,000 g/mole.

8. The bearing material of claim 7, wherein the molecular weight of the copolymer is about 12,600 g/mole.

9. The bearing material of claim 1, wherein the surface active agent is present in an amount of from about 0.5% to about 1% by weight of the bearing material.

10. The bearing material of claim 9, wherein the surface active agent is a nonionic surface active agent.

11. The bearing material of claim 10, wherein the nonionic surface active agent comprises a block copolymer of hydrophilic and hydrophobic blocks.

12. The bearing material of claim 11, wherein the block copolymer is an A-B, A-B-A, or B-A-B block copolymer, wherein A is a hydrophilic block and B is a hydrophobic block.

13. The bearing material of claim 12, wherein A is polyethylene oxide (PEO) and B is polypropylene oxide (PPO).

14. The bearing material of claim 13, wherein the molecular weight of the copolymer is from about 1000 to about 20,000 g/mole.

15. The bearing material of claim 14, wherein the molecular weight of the copolymer is 12,600 g/mole.

16. The bearing material of claim 3, wherein the surface active agent is present in an amount of from about 0.5% to about 1% by weight of the bearing material.

17. The bearing material of claim 4, wherein the surface active agent is present in an amount of from about 0.5% to about 1% by weight of the bearing material.

18. The bearing material of claim 5, wherein the surface active agent is present in an amount of from about 0.5% to about 1% by weight of the bearing material.

19. The bearing material of claim 6, wherein the surface active agent is present in an amount of from about 0.5% to about 1% by weight of the bearing material.

20. The bearing material of claim 7, wherein the surface active agent is present in an amount of from about 0.5% to about 1% by weight of the bearing material.

21. The bearing material of claim 8, wherein the surface active agent is present in an amount of from about 0.5% to about 1% by weight of the bearing material.

* * * * *

UNITED STATES PATENT AND TRADEMARK OFFICE
CERTIFICATE OF CORRECTION

| | | |
|---|---|---|
| PATENT NO. | : 7,812,098 B2 | Page 1 of 1 |
| APPLICATION NO. | : 11/394423 | |
| DATED | : October 12, 2010 | |
| INVENTOR(S) | : Ernsberger et al. | |

It is certified that error appears in the above-identified patent and that said Letters Patent is hereby corrected as shown below:

Column 6, Claim 6, Line 64, (PLO) should read --(PEO)--.

Signed and Sealed this
Twelfth Day of April, 2011

David J. Kappos
*Director of the United States Patent and Trademark Office*